(12) United States Patent
Zhao et al.

(10) Patent No.: US 7,564,544 B2
(45) Date of Patent: Jul. 21, 2009

(54) METHOD AND SYSTEM FOR INSPECTING SURFACES WITH IMPROVED LIGHT EFFICIENCY

(75) Inventors: Guoheng Zhao, Milpitas, CA (US); Zheng Yan, San Jose, CA (US); Bo Li, Palo Alto, CA (US); Wayne Chen, Palo Alto, CA (US)

(73) Assignee: 3i Systems Corporation, Sunnyvale, CA (US)

( * ) Notice: Subject to any disclaimer, the term of this patent is extended or adjusted under 35 U.S.C. 154(b) by 347 days.

(21) Appl. No.: 11/626,102

(22) Filed: Jan. 23, 2007

(65) Prior Publication Data

US 2007/0222974 A1 Sep. 27, 2007

(51) Int. Cl.
*G01N 21/00* (2006.01)
(52) U.S. Cl. .................... 356/237.2; 356/237.5
(58) Field of Classification Search ... 356/237.1–237.5, 356/601–623; 250/559.23, 559.29
See application file for complete search history.

(56) References Cited

U.S. PATENT DOCUMENTS

| | | | | |
|---|---|---|---|---|
| 5,024,529 | A | * | 6/1991 | Svetkoff et al. ............. 356/608 |
| 5,864,145 | A | * | 1/1999 | Krimermann et al. .. 250/559.29 |
| 5,883,714 | A | * | 3/1999 | Jann et al. .................... 356/484 |
| 6,046,812 | A | * | 4/2000 | Baik et al. ................... 356/613 |
| 6,714,283 | B2 | * | 3/2004 | Laurent et al. ............. 356/3.07 |
| 7,016,044 | B2 | * | 3/2006 | Murtagh et al. ............. 356/432 |
| 2005/0052643 | A1 | * | 3/2005 | Lange et al. ............. 356/237.1 |

\* cited by examiner

*Primary Examiner*—Hoa Q Pham
(74) *Attorney, Agent, or Firm*—Joe Zheng

(57) ABSTRACT

The radiation beam of discrete light source such as LEDs is shaped by a cylindrical lens and a spherical lens to form two perpendicular narrow lines to illuminate a surface. The first line is projected onto a sample surface to improve illumination efficiency, and the second line is projected onto a pupil plane of an imaging lens to improve illumination uniformity. The layout of the LED chip is optimized to match the aspect ratio of the imaging detector. Multiple LEDs at different wavelengths are combined to improve sensitivity. The full surface of the sample is inspected through the relative motion between the sample and the optics.

19 Claims, 9 Drawing Sheets

METHOD AND SYSTEM FOR INSPECTING SURFACES WITH IMPROVED LIGHT EFFICIENCY

BACKGROUND OF THE INVENTION

The invention is related in general to the area of inspection systems. In particular, the invention provides a method and system for inspecting printed patterns on a flat substrate, such as liquid crystal displays (LCD), flat panel displays (FPD), organic light emitting diode (OLED) substrates, masks and semiconductor wafers during a corresponding manufacturing process.

Automatic optical inspection (AOI) is a critical step in a manufacturing process of LCD and semiconductor IC chips for diagnosing and improving the yield of the production, thus reducing the manufacturing cost. The fundamental performance of AOI is measured by two key specifications: speed and sensitivity of inspection. The advances of manufacturing technology have lead to higher speed of fabrication, a larger size of substrate, and smaller dimensions of printed patterns, all of which result in a more demanding need for AOI with higher speed and better sensitivity.

The amount of light required for acquiring images of sample surfaces is inversely proportional to the area of the imaging pixel size and the speed of inspection, and inevitably, the high speed and high resolution inspection for LCD or wafer need high efficient illumination optics. Increasing imaging lens numerical aperture (NA) proportionally to the imaging pixel size could compensate for the increased demand for more lighting, but has a negative impact on the requirements of mechanical precision of the system due to the reduction of depth of focus. In addition, the NA of the imaging lens is often limited by a large field of view that is necessary for inspecting large sample surfaces. Conventionally the fiber line lights, or LED line lights are used for illumination when a line scan CCD camera is used to scan the surface of samples. Such illumination method and apparatus work well for low-resolution inspections, for example, with an image pixel size of larger than 10 um. The illumination technique becomes inefficient for high-resolution inspection, for example, for imaging pixel sizes of less than 10 um. The disadvantages of using a fiber line light include the low efficiency (typically 50% from one end to another end) of the total effective transmission of the fiber bundle, largely due to the gap between individual fibers, reflections of end surface and transmission loss in fibers. Fiber bundles are normally used with a lamp based light source. A lamp source has a short life time on the order of 1000 hours. Although the lamps can be replaced easily and cost effectively, the down time associated with replacing the lamp often includes re-calibration of the inspection tool, lasting several hours. In return, this has a significant impact on the cost of production where the production line is running continuously at high speed. Another disadvantage of using a lamp-based light source is that lamps generate light at a wide range of wavelengths. Since only a small range of the wavelengths is used for imaging, the light efficiency is further reduced when filters are used.

LEDs are more attractive as light sources for AOI. Their advantages include the high efficiency in generating light at desired wavelengths and very long lifetime in the order of tens of thousands of hours. However, the total amount of light output by a single LED chip is still much lower than a lamp, for example, a current high power single LED light source is rated at around a few watts, while most lamp light sources are rated at a few hundreds of watts. A conventional method of increasing the light intensity of LEDs for AOI is to densely package a large number of LED chips on a single printed circuit board, for example, the LED line lights supplied by Stockeryale (model of COBRA LED line light). However, the densely packaged LED chips result in excessive heat generation and a large package size due to the requirements of a large heat sink. Furthermore, the brightness (defined as the light power per unit area per unit solid angle) of the light source does not increase when more LED chips are added. The majority of light output is wasted when the optical invariant (defined by the product of the light emitting area and the solid angle of light output) of the light source largely exceeds the optical invariant of the imaging optics (defined by product of the field of view and NA).

Another disadvantage of using a fiber line array or LED chip array is the poor uniformity in illumination over a large field of view. The uniformity of illumination is largely determined by the transmission uniformity of each individual fibers, or variation between LED chips, and the geometric alignment errors of each chip.

One of the challenges associated with inspecting large samples, such as a 7th generation LCD glass substrate well over 2000 mm×2000 mm in size, is the footprint of the inspection tools. Fabrication clean rooms are expensive to construct and operate, thus smaller footprint equipments are highly desired.

Therefore, there is a need for highly efficient, long lifetime, compact and cost effective illumination method and apparatus for high resolution AOI of LCD glass substrate and semiconductor wafers.

SUMMARY OF THE INVENTION

This section is for the purpose of summarizing some aspects of the present invention and to briefly introduce some preferred embodiments. Simplifications or omissions in this section as well as in the abstract and the title may be made to avoid obscuring the purpose of this section, the abstract and the title. Such simplifications or omissions are not intended to limit the scope of the present invention.

The invention provides techniques for inspecting a substrate typically in large size, such as a LCD glass substrate or a semiconductor wafer. A discrete LED light source is used and the output of the LED light is shaped by illumination optics that matches the field of view and NA of a line scan imaging optics to achieve high efficiency and optimized uniformity. The illumination optics includes a spherical lens and a cylindrical lens, both of which form astigmatism images of the LED that are two perpendicular lines separated in space along an optics axis. The first line image of the LED is formed at the surface of a sample which is also considered as an object plane of the imaging lens to achieve high illumination efficiency. The second line image is formed at the pupil plane of the imaging lens to achieve both intensity uniformity and angular uniformity across the longer dimension of the field of view of the line scan imaging sensor. The longer direction of the line scan CCD or TDI is parallel to the first line of illumination. The shape of the LED chip can be further optimized to match the aspect ratio of the TDI sensor for maximum light efficiency.

The present invention may be implemented as a method, an apparatus or a part of system. According to one embodiment, the present invention is a system for inspecting a surface of a substrate, the system comprises: a line scan sensor; an imaging lens; and an illumination source, including a number of light sources, each at one wavelength, provided via at least two lenses to illuminate a surface of a substrate being inspected. Depending on an exact implementation the two lenses include: a cylindrical lens and a spherical lens to produce first and second lines from the illumination source, the first line projected on the surface and the second line projected in a perpendicular direction at a pupil plane of the imaging lens to achieve both intensity uniformity and angular uniformity across a field of view of the line scan sensor, and an image of the surface is focused onto the line scan sensor by the imaging lens.

According to another embodiment, the present invention is a system for inspecting a surface of a substrate, the system comprises a line scan sensor; an imaging lens; a front illumination source provided via at least two lenses to illuminate a surface of a substrate being inspected, a back illumination source to enhance detection of defects that are otherwise difficult to detect with only the front illumination source; and at least one vacuum preload air bearing chuck to provide a down force to stabilize the substrate during a high-speed motion of the substrate over air bearings.

One of the objects, features, advantages, benefits of the present invention is to provide method and systems for detecting defects on substrate with an improved illumination system.

Other objects, features, advantages, benefits of the invention will become more apparent from the following detailed description of a preferred embodiment, which proceeds with reference to the accompanying drawings

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE SPECIFIC EMBODIMENTS

The detailed description of the present invention is presented largely in terms of procedures, steps, logic blocks, processing, or other symbolic representations that directly or indirectly resemble the operations of devices or systems contemplated in the present invention. These descriptions and representations are typically used by those skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

Figure 1A:
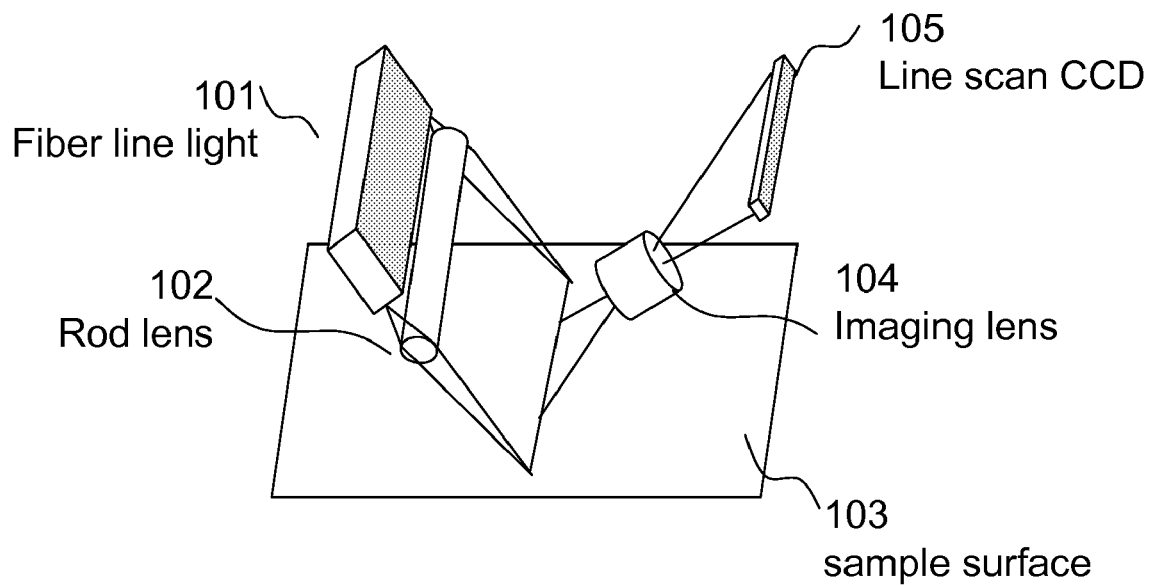
FIG. 1A is a schematic diagram of a prior art system using a fiber line light or a LED line array for illumination.
Figure 1B:
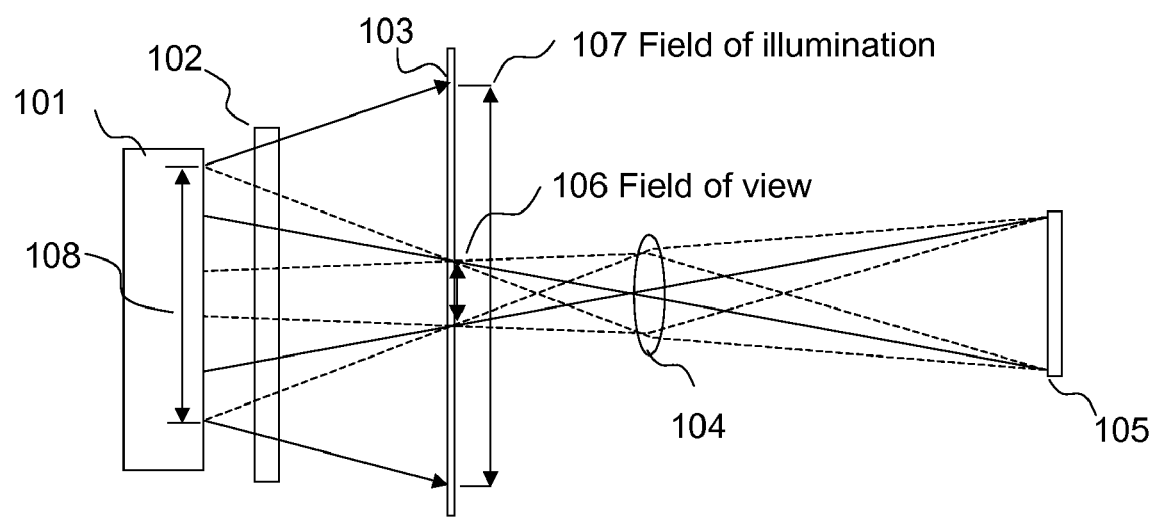
FIG. 1B is a detailed diagram of illumination field and imaging field of FIG. 1A.

Referring now to the drawings, in which like numerals refer to like parts throughout the several views. FIG. 1A shows a prior art system including an illumination source 101 and imaging optics 102 for inspecting a surface 103. A line scan CCD camera 105 is used to capture the image. The fiber line light (or a LED line light) 101 and a cylindrical lens 102 are used for projecting a narrow line of light onto the sample surface 103, and a portion of the illuminated field is imaged by a lens 104 onto the line scan CCD sensor 105. The image of the surface 103 is acquired when there is a relative motion between the sample surface 103 and the imaging optics 102. The image of the surface 103 is formed by the reflected light where the sample surface 103 acts as a mirror. However, the principal of illumination and imaging may be better illustrated by unfolding the optical path into a transmission mode as shown in FIG. 1B. The length of the fiber line light 101 is determined by the angle of field of view of the imaging lens 104, and the distance from the fiber line light to the sample. The field of illumination 107 is much longer than the length of the field of view of the imaging lens, due to the constrains of the field angle and illumination uniformity, therefore the illumination is very inefficient.

The disadvantages of the prior art system shown in FIG. 1 include the low light efficiency, large and heavy components, and excessive heat generation of the light source 101, therefore is not suitable in a moving scanning optics head. For inspection of a very large sample, such as an LCD glass substrate, it is advantageous to have an optics head move in at least one direction to image the whole surface by scanning motion to reduce the footprint of the inspection tool. Therefore it is highly desirable to have a compact, highly efficient, and long lifetime illumination system.

Figure 2A:
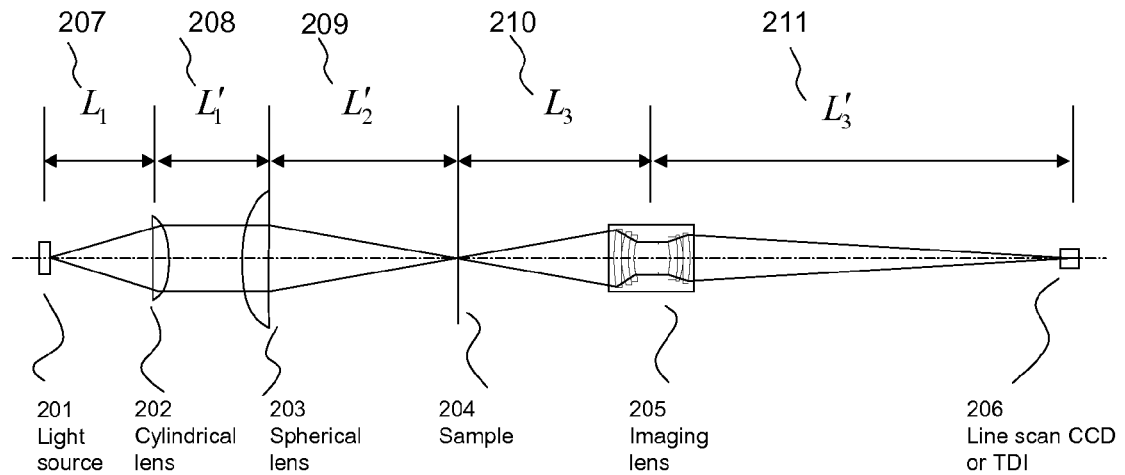
FIG. 2A is a schematic diagram of a top view of a new illumination technique using a discrete LED light source.
Figure 2B:
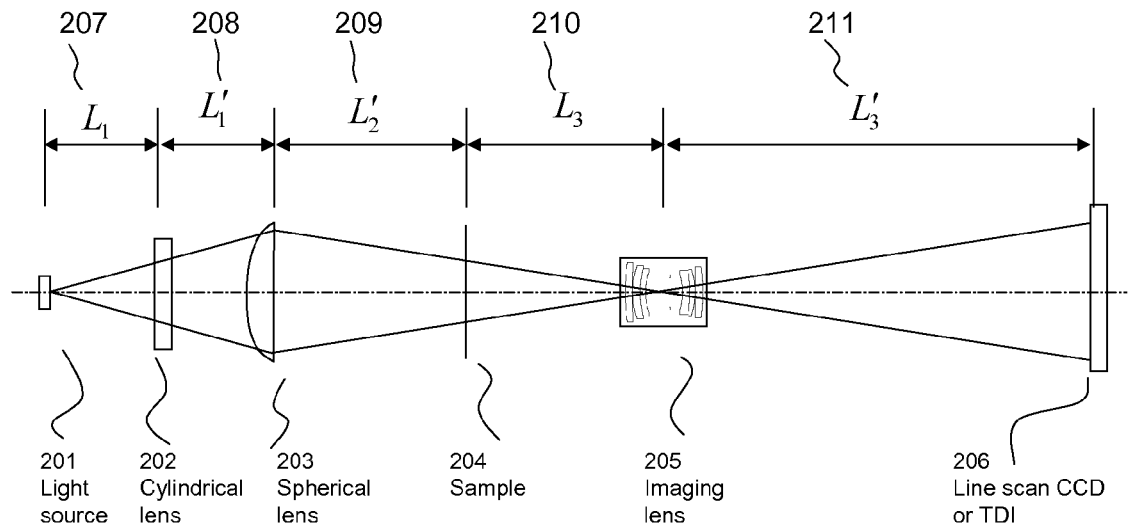
FIG. 2B is a schematic diagram showing a front view of FIG. 2A.

FIG. 2A and FIG. 2B show an exemplary embodiment of using a discrete LED light source for illuminating a surface with a line scan CCD camera or TDI camera. Both are respectively presented from a top perspective and a front perspective. As shown in the figure, a pair of cylindrical lens 202 and spherical lens 203 is provided to shape the output of a discrete LED light 201. For optimum illumination uniformity and efficiency, the focal lengths of the lenses 202 and 203 and the distance therebetween are designed according to the following equations.

It is assumed that the LED 201 is located at a distance $L_1$ 207 from the cylindrical lens 202 having a focal length of $f_1$, where $$L_1 = f_1 \tag{1}$$

The light is collimated in one dimension by the cylindrical lens 202, and focused by the spherical lens 203 having a focal length of $f_2$ into a line that is parallel to the longer axis of the cylindrical lens 202. The distance $L_1'$ from the spherical lens 203 to the cylindrical lens 202 is given by:

$$\frac{1}{L_1' + L_1} + \frac{1}{L_2' + L_3} = \frac{1}{f_2} \tag{2}$$

such that in the direction perpendicular to the longer axis of the cylindrical lens 202, a real image of the LED light source 201 formed by the spherical lens 203 (when the cylindrical lens 202 is not present) is located at the pupil plane of the imaging lens 205, as shown in FIG. 2B. The distance 209 from the spherical lens 203 to the sample 204 is given by:

$$L_2' = f_2 \tag{3}$$

and the distance 210 from the sample 204 to the pupil plane of imaging lens 205 is given by:

$$\frac{1}{L_3} + \frac{1}{L_3'} = \frac{1}{f_3} \tag{4}$$

such that a real image of the sample is formed by the imaging lens onto the surface of the CCD sensor 206.

The optical magnification is determined by the CCD sensor element size $p_c$ and the optical imaging pixel size $p_s$ on the sample:

$$M = \frac{p_c}{p_s} \tag{5}$$

and the full field of view (FFOV) is given by:

$$FFOV = N p_s \tag{6}$$

where N is the number of elements in the CCD sensor.

The full field angle (FFA) is thus given by:

$$FFA = \frac{FFOV}{L_3} \tag{7}$$

The minimum diameter D of the spherical lens 208 is given by the FFA and the NA of the imaging lens 205 through the following equation to ensure that the illumination covers both the full field of view and the full field angle of the imaging lens:

$$D = (L_3 + L_2') FFA + 2 L_2' \cdot NA \tag{8}$$

The focal length $f_1$ of cylindrical lens 202 and focal length $f_2$ spherical lens 203 are chosen to give the optimized magnification for maximum illumination efficiency. The length of the line projected onto the pupil stop of the imaging lens 205 is closely matched to the diameter of the stop aperture, and preferably smaller than the stop diameter. The converging angle in the direction perpendicular to the line projected onto the sample plane 204 is matched to the NA of the imaging lens 205, and preferably smaller than the NA of the imaging lens.

Figure 3:
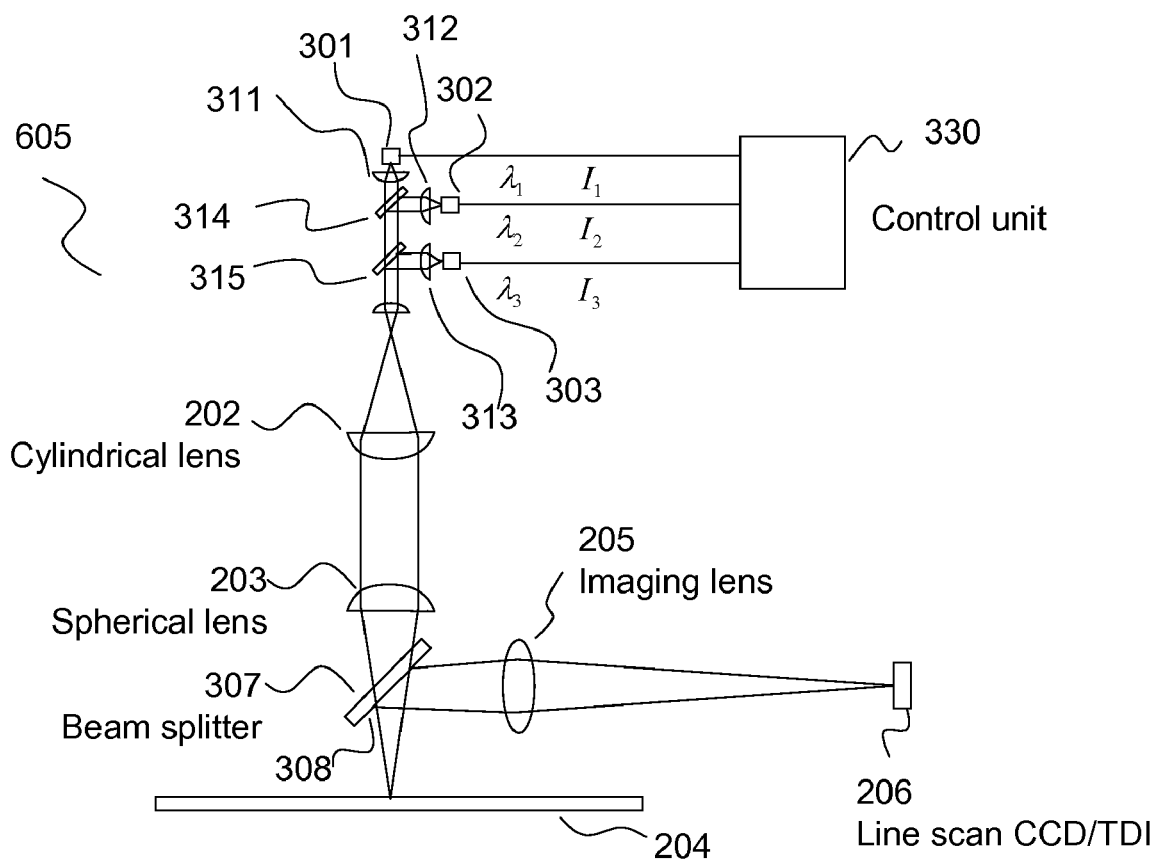
FIG. 3 is a schematic diagram of combining multiple LED light sources of different wavelengths, according to one embodiment of the present invention.

FIG. 3 is a schematic configuration showing an exemplary embodiment of using multiple LED light sources at different wavelengths for inspecting a flat surface. Though three LEDs at three different wavelengths are shown in the drawing, other numbers of wavelengths may be used. The LED 301 generates light at wavelength $\lambda_1$, LED 302 generates light at wavelength $\lambda_2$, and LED 303 generates light at wavelength $\lambda_3$. The output lights of the LEDs are collimated by lenses 311, 312, and 313, and combined by dichroic beam splitters 314 and 315. The dichroic beam splitter 314 reflects the light at wavelength $\lambda_2$ and transmits the light at wavelength $\lambda_1$. The dichroic beam splitter 315 transmits the lights at wavelengths $\lambda_1$ and $\lambda_2$, and reflects the light at wavelength $\lambda_3$. A control unit 330 independently controls the intensities of the light at the three wavelengths. The light intensity illuminating the sample surface is given by $$I = I_1 + I_2 + I_3 \tag{9}$$

where $I_1$, $I_2$, and $I_3$ are the output intensity of LED light sources at wavelengths of $\lambda_1$, $\lambda_2$, and $\lambda_3$ respectively.

Each of the light intensity of $I_1$, $I_2$, and $I_3$ is adjustable from 0 to 100% of the total light intensity to optimize for defect detection sensitivity on different sample surfaces. For example, both the optical properties and thickness of a thin film coating on a substrate affect the reflectivity differently at different wavelength, and as a result, some wavelengths have better defect detection sensitivity than other wavelengths. The adjustable combination of the relative intensities of different wavelengths allows optimization of defect detection sensitivity, which is very difficult to implement with a conventional fiber line light.

In addition, the continuously adjustable relative weights of each wavelength allows to compensate for the non-uniform transmission of the optical system and the non-uniform spectral response of the CCD sensor to achieve a true flat illumination spectrum, which is desirable in inspecting the surface that has higher noise induced by film thickness variations. Dark field illumination and imaging (not shown in FIG. 3) can also be implemented by adding another light source, preferably a laser, to illuminate the surface at an angle from the normal to the surface.

The imaging lens 205 is positioned in the reflection path of the beam splitter 307, and the beam splitter 307 is so oriented that the beam splitting surface 308 is towards the imaging lens 205 and the light ray from the sample surface 204 does not pass through the beam splitter 307, therefore any aberrations induced by the thickness of the beam splitter is eliminated.

LEDs are generally incoherent light sources, and have the characteristics of emitting light into a large solid angle. In addition, the light emitting area has a finite size, typically in millimeters for high power LEDs. For high speed line scan inspection, the CCD sensors are generally line scan CCDs or high sensitivity TDI sensors. A line scan CCD has one row of elements (photo sensors), for example, DALSA line scan CCD model number P3-80-08k40 has 8192 elements, the aspect ratio of imaging field is therefore 8192:1. TDI sensors has multiple rows of elements to enhance light sensitivity, however, due to manufacturing cost and yield limitation, the number of rows is normally limited. For example, DALSA TDI sensor model number HS-80-08k80 has 96 rows of elements, and each row has 8192 elements, therefore the aspect ratio of imaging field is approximately 85:1. The highly asymmetric shape of the sensors requires further optimization of the shape and layout of the light emitting area to improve illumination light efficiency and uniformity.

Figure 4A:
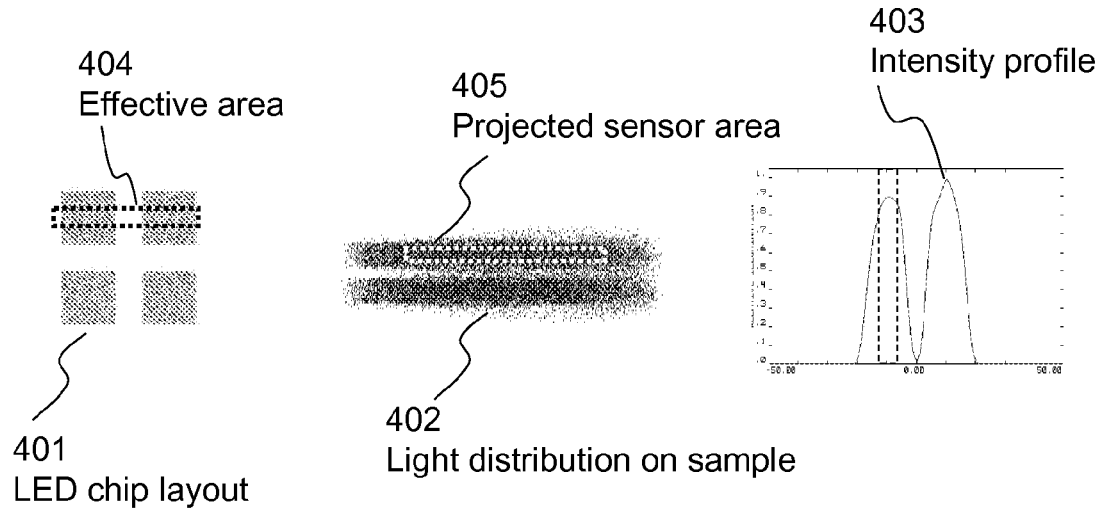
FIG. 4A is a schematic diagram of an exemplary layout of a commercial LED chip dimension.
Figure 4B:
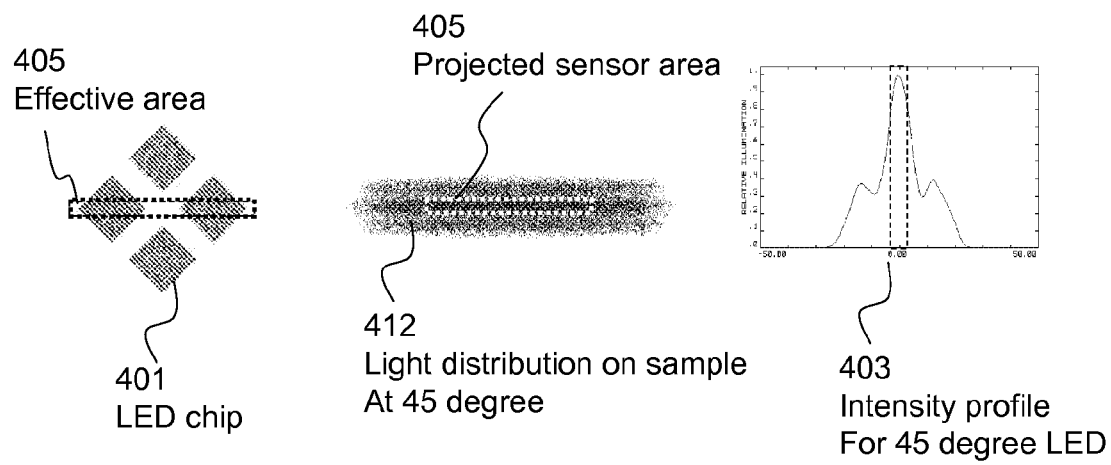
FIG. 4B shows an optimized orientation of a LED chip for illuminating the optical field of view of a line scan CCD or TDI.

FIG. 4A shows an example of the layout of the light emitting area of a high power LED (for example, model Luxeon V star supplied by LUMILEDS). The light emitting area includes four squared light emitting chips 401 positioned symmetrically within an area of approximately 2×2 mm. The light distribution 402 on a sample surface generated by the illumination optics shown in FIG. 2 will be in two lines, each generated by the top and bottom pair of light emitting chips when one of edges of the chip 401 is parallel to the long axis of the cylindrical lens 202. Although the illumination optics of the present invention has optimized the light efficiency of illumination for the line scan CCD sensor, due to the very high aspect ratio of the line scan CCD sensor, the width of the illumination line is normally much wider than the width of the imaging field, which is the projected area 405 of the sensor onto the sample. Therefore only one of the line formed on the surface may be imaged onto the CCD sensor. The intensity profile 403 is also shown in FIG. 4A to illustrate the portion of light (indicated by the rectangular dotted line) that is used for imaging. Effectively, only the light from the area 404 of LED is used.

To improve light efficiency, in one embodiment, the LED is rotated by 45 degrees such that the diagonal direction of the LED chip is aligned with the longer axis of the cylindrical lens. As a result, the light distribution on the sample consists of one strong central line and two weaker side lobes. The effective area useful for illumination is the area 405, which is approximately 40% greater than the effective area 404 due to the fact that the diagonal dimension is 1.4 times the edge of a square.

Figure 5A:
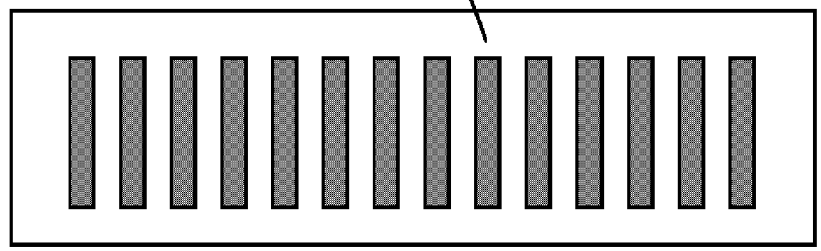
FIG. 5A to FIG. 5D are respective examples of the layout of the light emitting area of LED chips optimized for use in the illumination and imaging optics configuration in FIG. 2.
Figure 5B:
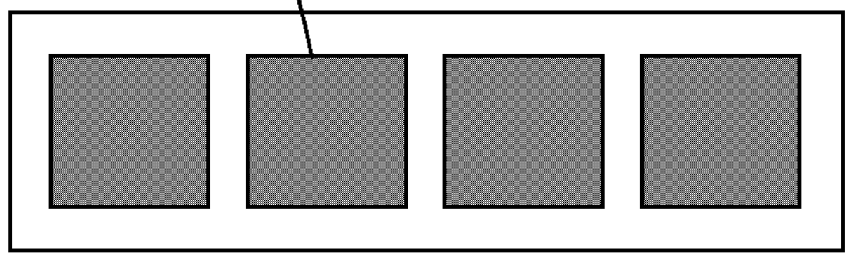

The LED light emitting area can be further optimized for the line scan application. FIG. 5A shows the layout of LED light emitting area optimized for line scan illumination. The light emitting area 501 includes an array of narrow strips, and the gaps between the light emitting strips are used for placement of electrodes. The overall area of the light emitting area is optimized to match the aspect ratio of the elongated imaging sensor. FIG. 5B is another LED light emitting area layout includes a linear array of rectangular light emitting elements 502. The overall length and width of the array is matched to the aspect ratio of the line scan CCD or TDI sensor.

Figure 5C:
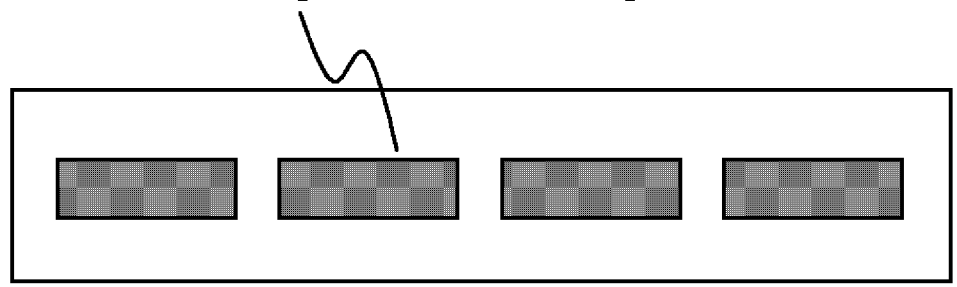
Figure 5D:
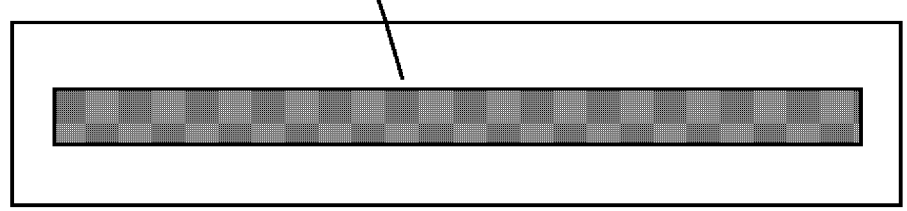

FIG. 5C is yet another layout of an LED light emitting area that includes a linear array of rectangular light emitting elements 503, and the length and width of the array are matched to the aspect ratio of a line scan CCD or TDI. FIG. 5D is yet another layout of an LED light emitting area that includes a continuous rectangular light emitting area 504, and the length and width of the light emitting area are matched to the aspect ratio of a line scan CCD or TDI sensor. Other forms of layout, where the details of the light emitting area may be different, but the total light emitting area is designed to match the aspect ratio of a line scan CCD or TDI sensor, are within the scope of the invention.

Figure 6:
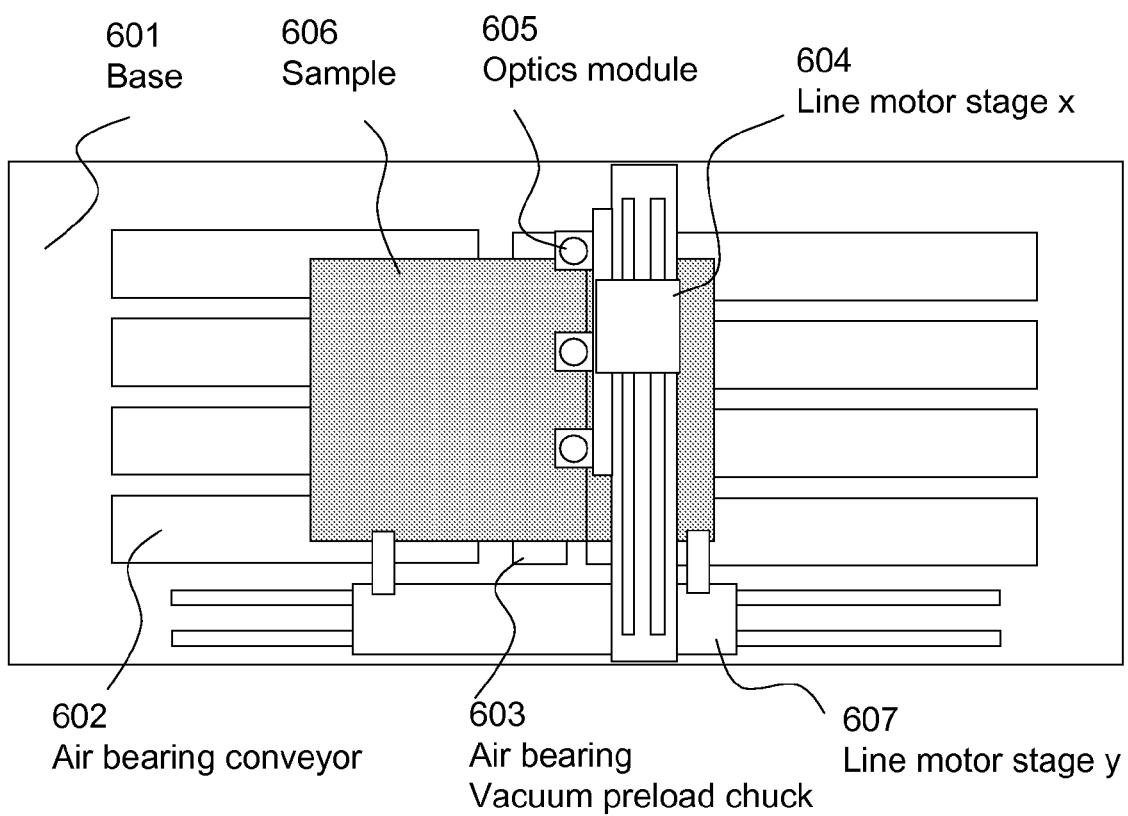
FIG. 6 is a diagram of an embodiment using the LED illumination for high speed inspection of large surfaces.

FIG. 6 is a schematic layout of inspecting large a flat surface such as a LCD glass substrate 606. The optics module 605 includes illumination and imaging components that have been shown in FIG. 3. The longer direction of the imaging field is parallel to the motion axis of linear stage (stage x) 604. The glass substrate 606 moves in the direction parallel to the linear stage Y 607, and is supported by an air bearing conveyor 602 and vacuum preload air bearing chuck 603. The vacuum preload of the air bearing chuck 603, such as one supplied by Newway airbearing model number S2225401, provides high rigidity for the glass during motion on top of a thin layer of air. The linear motor stage 604 moves the optics module one step of the field size at a time, every time when the glass moves a full length in the perpendicular direction until the full area of the glass is inspected.

Figure 7:
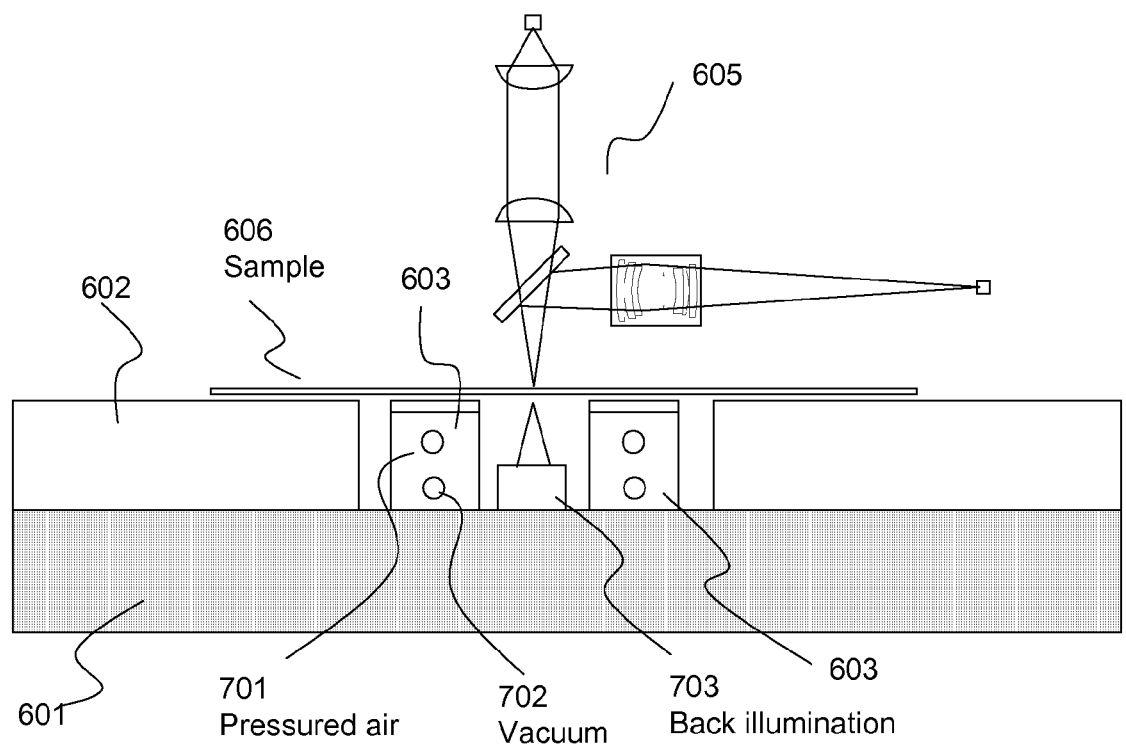
FIG. 7 is a sectional view of the system of FIG. 6.

FIG. 7 is a side section view of the configuration shown in FIG. 6 to show a backside illumination 703 to enhance detection of defects that are otherwise difficult to detect with front side illumination. Two vacuum preload air bearing chucks 603 are used, the gap between the chucks provides a space for backside illumination. The chucks have a vacuum outlet 702 and a pressure air input 701. The vacuum provides a down force to stabilize the glass during high-speed motion on air bearing.

Figure 8:
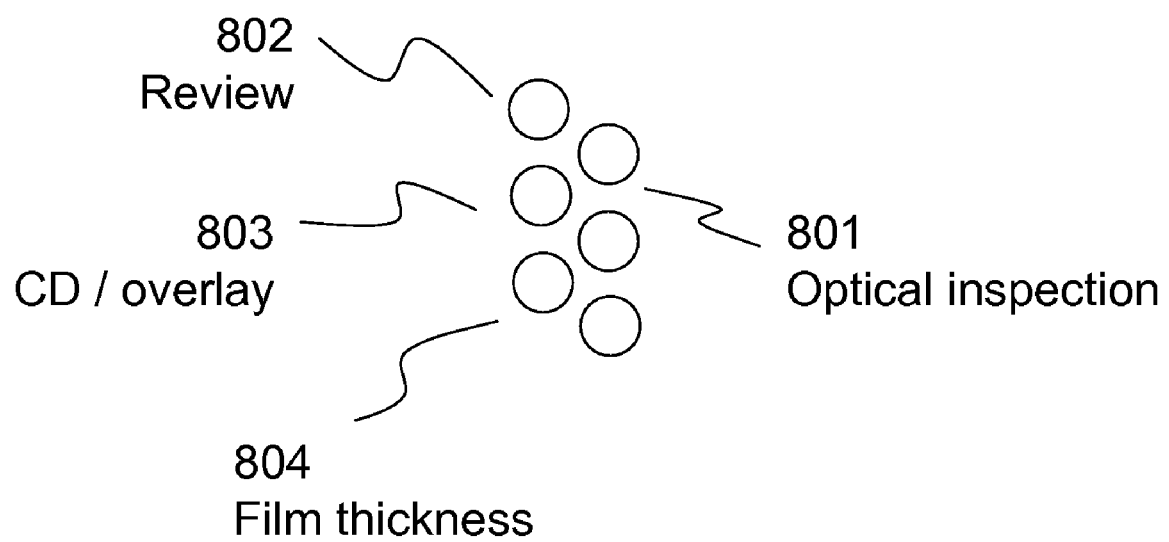
FIG. 8 is a diagram of combining multiple optics modules with different inspection and metrology functions.

FIG. 8 shows a combination of optics modules with different inspection and metrology functions. Multiple optics inspection modules 801 are combined with an optics review microscope 802, a critical dimension (CD) measurement and overlay measurement module 803, and a thin film thickness measurement module 804, such that both defect inspection and optical metrology can be performed on the same tool.

The present invention has been described in sufficient details with a certain degree of particularity. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the foregoing description of embodiments.

We claim:

1. A system for inspecting a surface of a substrate, the system comprising:
 a line scan sensor;
 an imaging lens; and
 an illumination source including a number of light sources at different wavelengths, output lights of the light sources collimated respectively and then combined by at least one dichroic beam splitters, each of the light sources being adjustable to optimize for defect detection sensitivity on the surface of the substrate, the combined light being provided via at least two lenses to illuminate the surface of the substrate being inspected, wherein the two lenses include:
 a cylindrical lens and a spherical lens to produce first and second illumination lines from the combined light, the first illumination line projected on the surface and the second illumination line projected in a perpendicular direction at a pupil plane of the imaging lens to achieve both intensity uniformity and angular uniformity across a field of view of the line scan sensor, wherein an image of the surface is focused onto the line scan sensor by the imaging lens.

2. The system as recited in claim 1, wherein the line scan sensor is a COD or a TDI sensor.

3. The system as recited in claim 1, further comprising:
 an air bearing conveyor transporting the substrate; and a moving mechanism to cause a relative movement of the substrate with respect to the system.

4. The system as recited in claim 3, further comprising a vacuum preload air bearing chuck to support and stabilize the substrate under the field of view of the line scan sensor.

5. The system as recited in claim 1, wherein the light sources include at least a first LED to generate a light at wavelength $\lambda_1$ and a second LED to generate a light at wavelength $\lambda_2$, the light from the first or second LED is collimated and combined by a dichroic beam splitter.

6. The system as recited in claim 5, wherein each of the first or second LED includes an LED light emitting area formed by an array of narrow strips, and gaps between the light emitting strips are used for placement of electrodes, an overall area of the light emitting area is optimized to match an aspect ratio of an elongated imaging sensor in the line scan sensor.

7. The system as recited in claim 6, further including a control unit configured to independently control a corresponding intensity of the light at wavelength $\lambda_1$ or $\lambda_2$.

8. The system as recited in claim 6, wherein the intensity of the light at wavelength $\lambda_1$ or $\lambda_2$ is adjustable to optimize for defect detection sensitivity based on characteristics of the surface of the substrate.

9. The system as recited in claim 1, wherein the light sources are arranged substantially in a squared array that is rotated by 45 degrees such that a diagonal direction of the squared array is aligned with a longer axis of the cylindrical lens, as a result, light distribution on the surface of the substrate includes one strong central line and two weaker side lobes.

10. The system as recited in claim 1, wherein the substrate is one of liquid crystal displays (LCD), flat panel displays (FPD), organic light emitting diode (OLED) substrates, masks and semiconductor wafers.

11. The system as recited in claim 1, further comprising a dark field illumination positioned at an angle from a normal to the surface.

12. A system for inspecting a surface of a substrate, the system comprising:
   a line scan sensor;
   an imaging lens;
   a front illumination source including a number of light sources at different wavelenths, output lights of the light sources respectively collimated and then combined by at least one dichroic beam splitters, each of the light sources being adjustable to optimize for defect detection sensitivity on the surface of the substrate, the combined light being provided via at least two lenses to illuminate the surface of the substrate being inspected, wherein the two lenses include:
      a cylindrical lens and a spherical lens to produce first and second lines from the illumination source, the first line projected on the surface and the second line projected in a perpendicular direction at a pupil plane of the imaging lens to achieve both intensity uniformity and angular uniformity across a field of view of the line scan sensor, and an image of the surface is focused onto the line scan sensor by the imaging lens;
   a back illumination source to enhance detection of defects that are otherwise difficult to detect with only the front illumination source; and
   at least one vacuum preload air bearing chuck to provide a down force to stabilize the substrate during a high-speed motion of the substrate over air bearings.

13. The system as recited in claim 12, further comprising a moving mechanism to cause a relative movement of the substrate with respect to an inspection module that includes the line scan sensor; the imaging lens; the front and back illumination sources, and a control unit to control intensity of light sources in the front and back illumination sources.

14. The system as recited in claim 13, wherein the light sources include at least a first LED to generate a light at wavelength $\lambda_1$ and a second LED to generate a light at wavelength $\lambda_2$, the light from the first or second LED is collimated and combined by a dichroic beam splitter.

15. The system as recited in claim 14, wherein the dichroic beam splitter reflects the light at wavelength $\lambda_2$ and transmits the light at wavelength $\lambda_1$.

16. The system as recited in claim 12, wherein an intensity of the light at wavelength $\lambda_1$ or $\lambda_2$ is adjustable to optimize for defect detection sensitivity based on characteristics of the surface of the substrate.

17. The system as recited in claim 12, wherein the light sources in the front illumination source are arranged substantially in a squared array that is rotated by 45 degrees such that a diagonal direction of the squared array is aligned with a longer axis of the cylindrical lens, as a result, light distribution on the surface of the substrate includes one strong central line and two weaker side lobes.

18. The system as recited in claim 12, wherein the substrate is one of liquid crystal displays (LCD), flat panel displays (FPD), organic light emitting diode (OLED) substrates, masks and semiconductor wafers.

19. The system as recited in claim 12, further comprising a dark field illumination positioned at an angle from a normal to the surface.

* * * * *